United States Patent [19]

Brown et al.

[11] 4,036,592

[45] July 19, 1977

[54] DETECTION OF CARBON MONOXIDE

[75] Inventors: David Keith Brown; David William Dabill; Jack Graham Firth; Alan Jones; Thomas Alwyn Jones, all of Sheffield, England

[73] Assignee: National Research Development Corporation, London, England

[21] Appl. No.: 581,697

[22] Filed: May 28, 1975

[30] Foreign Application Priority Data

June 5, 1974 United Kingdom .............. 25045/74

[51] Int. Cl.$^2$ .................... G01N 27/16; G01N 31/12; H01C 3/00

[52] U.S. Cl. ................. 23/232 E; 23/254 E; 60/276; 73/27 R; 324/71 R; 324/71 SN; 338/13; 338/22 R; 423/213.5

[58] Field of Search ............ 23/232 R, 232 E, 254 R, 23/25 HE, 255 R, 255 E; 324/71 SN, 71 R, 98, DIG. 1; 338/13, 22, 34; 60/276; 73/27 R; 423/213.5; 252/472

[56] References Cited

U.S. PATENT DOCUMENTS

| 2,768,069 | 10/1956 | Thompson | 23/232 E UX |
| 3,560,160 | 2/1971 | Lanneau | 23/232 R |
| 3,865,550 | 2/1975 | Bott et al. | 23/232 E |
| 3,871,827 | 3/1975 | Seiler et al. | 23/232 R X |
| 3,893,230 | 7/1975 | Stadler et al. | 23/254 E X |

FOREIGN PATENT DOCUMENTS

| 225,210 | 7/1925 | United Kingdom |
| 892,530 | 3/1962 | United Kingdom |
| 1,105,046 | 3/1968 | United Kingdom |

Primary Examiner—Norman Yudkoff
Assistant Examiner—Barry I. Hollander
Attorney, Agent, or Firm—Cushman, Darby & Cushman

[57] ABSTRACT

In a catalytic method for selectively detecting carbon monoxide in the presence of hydrogen in an oxygen-containing atmosphere, such as may be used in monitoring exhaust gases from combustion processes, the catalyst is a platinum-rhodium alloy containing not less than about 10% rhodium. The catalyst is maintained at a temperature such that it will cause combustion of carbon monoxide but will not readily cause combustion of hydrogen, the thermal effect on the catalyst resulting when a test atmosphere is brought into contact with it being sensed to provide a measure of the carbon monoxide concentration in that atmosphere.

9 Claims, 4 Drawing Figures

DETECTION OF CARBON MONOXIDE

This invention relates to methods of gas detection of the kind in which an oxygen-containing atmosphere is tested for the presence of a specific combustible gas by bringing the atmosphere into contact with a catalyst maintained at a temperature such that it is capable of causing combustion of the specific gas, and sensing any thermal effect on the catalyst caused by the occurrence thereon of a combustion reaction. In one arrangement commonly used in methods of this kind, the catalyst is in the form of a wire which is heated to the required temperature by the passage through it of an electric current, the relevant thermal effect being sensed either by detecting changes in the resistance of the wire resulting from changes in its temperature or by detecting changes in the magnitude of the heating current necessary to maintain the wire at a given temperature. In another commonly used arrangement, disclosed for example in British Patent Specification No. 892,530, the catalyst is in the form of a surface coating or impregnation of a pellet of refractory material within which is embedded a coil of wire used for heating and thermal sensing in a manner similar to that applicable where the catalyst is itself in the form of a wire.

The catalyst materials conventionally used with such arrangements are platinum and palladium, but in cases where it is desired to employ a method of the kind specified for the quantitative measurement of carbon monoxide concentration the use of these conventional catalyst materials in a straightforward manner may be made difficult or impossible by the presence of hydrogen in the atmosphere under test; typical examples of applications in which this consideration applies are the monitoring of exhaust gases from internal combustion engines and the analysis of flue gases from heating appliances. The difficulty (which is discussed for example in British Patent Specification No. 1,105,046) arises because hydrogen is more readily oxidised than carbon monoxide on platinum and palladium, and is aggravated by the fact that the thermal effect of combustion on the catalyst is several times greater for a given concentration of hydrogen than for the same concentration of carbon monoxide.

In U.S. Pat. No. 3,560,160 there is disclosed a method of the kind specified in which the selective detection of carbon monoxide in the presence of hydrogen is effected by the use of the catalyst material known as hopcalite, which is maintained at a temperature such that it is capable of causing combustion of carbon monoxide but not of hydrogen. The use of this material, however, suffers from disadvantages. Firstly if it is maintained at a temperature sufficiently low to ensure relatively high sensitivity for the detection of carbon monoxide its catalytic activity is liable to be affected by the presence of water vapour in the atmosphere under test, so that it is necessary to provide means for drying this atmosphere before it reaches the catalyst; secondly the material, which is an amorphous mixture of metal oxides, does not lend itself readily to the fabrication of simple and cheap forms of gas-sensitive element such as are normally employed when using platinum or palladium as catalyst materials in the commonly used arrangements discussed above.

The present invention is based on the surprising discovery that platinum base alloys containing rhodium in a proportion of not less than about 10% by weight behave in a significantly different manner from platinum and palladium in respect of their abilities to catalyse the oxidation of carbon monoxide and hydrogen. In particular it is found that for such an alloy there is a range of temperatures (which varies with the rhodium content of the alloy) over which the alloy will cause combustion of carbon monoxide but will not readily cause combustion of hydrogen. This fact has not previously been appreciated, although it has long been known (for example from British Patent Specification No. 225,210) that various alloys of metals of the platinum group, including platinum-rhodium, may be used for the catalytic detection of combustible gases.

According to a first aspect of the invention, therefore, there is provided a method of gas detection of the kind specified, in which the specific combustible gas is carbon monoxide, the catalyst is a platinum base alloy containing rhodium in a proportion of not less than about 10% by weight, and the catalyst is maintained at a temperature such that it will not readily cause combustion of hydrogen in the atmosphere under test.

The use of the relevant platinum-rhodium alloys in method of the kind specified does not suffer from the disadvantages discussed above in connection with hopcalite, since at appropriate operating temperatures these alloys are not affected by the presence of water vapour in the atmosphere under test, and they can readily be used in similar ways to platinum and palladium in the fabrication of gas-sensitive elements. The alloys in question have relatively high thermal coefficients of resistivity, so that they are particularly suitable for use in arrangements of the kind previously mentioned in which the catalyst is in the form of a wire.

According to a second aspect of the invention, there is provided an apparatus for use in a method of gas detection of the kind specified, the apparatus comprising a catalyst exposed for contact with an atmosphere to be tested and consisting of a platinum base alloy containing rhodium in a proportion of not less than about 10% by weight, means for heating the catalyst to a temperature such that when an atmosphere containing oxygen, carbon monoxide and hydrogen is brought into contact with the catalyst it will cause combustion of carbon monoxide but will not readily cause combustion of hydrogen, and means for sensing any thermal effect on the catalyst caused by the occurrence thereon of a combustion reaction.

The invention will be further described and explained with reference to the accompanying drawings, in which.

Figure 1:
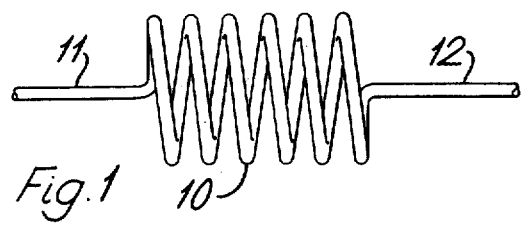
FIG. 1 shows in elevation a first form of gas-sensitive element.

The element shown in FIG. 1 consists of a length of wire whose central portion is shaped to form a coil 10, with the free ends 11 and 12 of the wire extending parallel to the axis of the coil 10 so as to enable the coil 10 to be readily connected in an electrical circuit. Typically the wire may have a diameter of 0.05 mm, and the coil 10 may consist of six turns of pitch 0.125 mm and diameter 0.5 mm. For use in conventional methods of gas detection the wire would normally be of platinum, but for use in a method according to the invention it will of course be of an appropriate platinum-rhodium alloy. Wires of suitable alloys may readily be obtained commercially, but it should be noted that such commercially available wires exhibit some variability in their behaviour in respect of the catalytic oxidation of carbon monoxide and hydrogen, it being found that different elements made from nominally the same wire may catalyse the relevant reactions at different temperatures. Studies carried out by Auger spectrometry suggest that such variability is due to the presence of an oxide on the surface of the wire. It can in any case readily be eliminated by a simple pretreatment involving heating the wire before use to a temperature in the range 900°–1200° C for at least 5 minutes; this heating may conveniently be done in air.

In use the coil 10 is connected in an electrical circuit (for example such as is described below with reference to FIG. 4) operative to pass an appropriate heating current through the coil 10 and to sense any changes in its resistance which result from changes in its temperature while it is exposed to an atmosphere under test. Table I below summarises results obtained in this way for elements of platinum and three different compositions of platinum-rhodium alloy. The results given in the second column were obtained using a test atmosphere of air having added to it a few percent by volume of carbon monoxide and the results given in the third column were obtained using a test atmosphere of air having added to it less than 2% by volume of hydrogen.

TABLE I

| Concentration of rhodium in platinum (weight %) | Temperature at which carbon monoxide oxidation begins (° C) | Temperature at which hydrogen oxidation begins (° C) |
| --- | --- | --- |
| 0 | 200 | 40 above |
| 10 | 200 | 600 |
| 20 | 170 | 370 |
| 40 | 150 | 270 |

At first sight the results quoted in Table I would suggest a preference for the wire composition containing 10% rhodium, in that it exhibits the largest temperature difference between commencement of oxidation of carbon monoxide and of hydrogen. This suggestion is, however, negatived by the results of further tests using atmospheres containing significant concentrations of both carbon monoxide and hydrogen; these results indicate that of the alloy compositions specified in Table I the most suitable for use in a method according to the invention is that containing 40% rhodium, since the others tend to be more likely to oxidise hydrogen in atmospheres containing carbon monoxide even though they do not oxidise hydrogen in the absence of carbon monoxide. Whichever alloy composition is used in a method according to the invention, the basic operating temperature of the element will of course be chosen to lie between the relevant values in the second and third columns of Table I. It will usually be preferable to choose a temperature nearer the lower than the upper end of the relevant range, and in some cases account may need to be taken of possible components of the atmosphere under test other than those mentioned above; in this connection it may be noted that for all the alloy compositions listed in Table I catalytic oxidation of hydrocarbons does not occur at temperatures below 400° C. In the case of the preferred composition containing 40% rhodium the basic operating temperature for the gas-sensitive element may suitably be about 200° C. Under these conditions the heat of the combustion reaction involving carbon monoxide is such that the temperature of the element will increase from its basic value by about 5° C for each one percent by volume of carbon monoxide in the atmosphere under test.

A further consideration that should be noted is that for concentrations of hydrogen in air greater than about 2% by volume some oxidation of hydrogen may occur at temperatures below those indicated for the respective platinum - rhodium alloys in the third column of Table I. Moreover if the oxygen concentration in the test atmosphere to which the gas-sensitive element is exposed is below the normal concentration in air there is a corresponding reduction in the limit of hydrogen concentration below which there is no significant oxidation of hydrogen; thus for values of the oxygen concentration down to about 10% by volume this limit of hydrogen concentration is approximately one tenth of the oxygen concentration but for lower values of oxygen concentration the hydrogen concentration limit decreases more rapidly than in proportion to the oxygen concentration. It is therefore desirable to ensure that in a method according to the invention the test atmosphere brought into contact with the catalyst contains at least 10% by volume of oxygen and that the hydrogen concentration in this atmosphere is less than one tenth of the oxygen concentration.

In cases where the invention is applied to the measurement of carbon monoxide concentration in an exhaust gas mixture resulting from a combustion process, it is necessary for the test atmosphere actually brought into contact with the catalyst to be produced by mixing the exhaust gas mixture with air in order to provide sufficient oxygen for the complete combustion of the carbon monoxide, whose concentration in such an exhaust gas mixture can be as high as 5–6% by volume. For this purpose it will normally be desirable to use a value of about three for the volumetric proportion of air to exhaust gas mixture, giving an oxygen concentration of about 15% by volume in the test atmosphere, and as a result the hydrogen concentration in the test atmosphere will normally be well below the relevant limit value, since the hydrogen concentration in the exhaust gas mixture will not normally exceed about 3% by volume. In such cases, therefore, the desiderata mentioned above concerning the composition of the test atmosphere will normally be met automatically without the need for any extra precautions.

Figure 2:
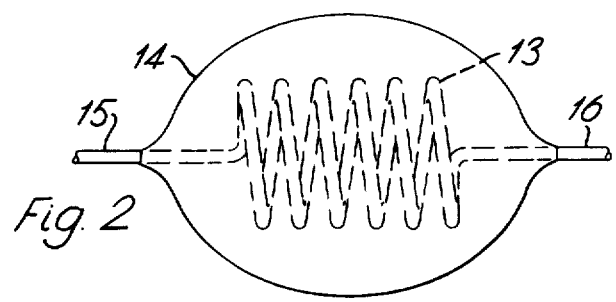
FIG. 2 shows in elevation a second form of gas-sensitive element.

In the gas-sensitive element shown in FIG. 2, a wire coil 13 similar to the coil 10 shown in FIG. 1 is embedded in a fused glass bead 14, except for its free ends 15 and 16. The bead 14 may be formed by dipping the coil 13 into a slurry of powdered glass in glycerol and passing an electric current through the coil 13 to evaporate the glycerol and melt the glass. Suitable types of glass are G.S. 10 glass of composition 82.8% $SiO_2$; 5.0% $Al_2O_3$; 11.8% $B_2O_3$; 0.4% BaO; or A43 glass of composition 54.3% $SiO_2$; 21.0% $Al_2O_3$; 8.0% $B_2O_3$; 13.5% CaO; 3.1% BaO; or a standard borosilicate glass.

For such an element it has been found that if the wire is of an appropriate platinum-rhodium alloy a temperature can be chosen at which in an oxygen-containing atmosphere the element will cause combustion of carbon monoxide but will not readily cause combustion of hydrogen. This somewhat surprising result is believed to be explicable on the basis that some of the metal of the wire is dissolved into the glass during the fusion process and subsequently migrates to the exposed surface of the glass. Table II gives the relevant temperatures for three types of glass, with alumina for comparative purposes, the wire being of 10% rhodium in platinum alloy in each case.

TABLE II

| Bead Material | Temperature at which carbon monoxide oxidation begins (° C) | Temperature at which hydrogen oxidation begins (° C) |
|---|---|---|
| G.S. 10 glass | 315 | above 600 |
| A43 glass | 400 | above 500 |
| Borosilicate glass | 400 | above 500 |
| Alumina | above 670 | above 670 |

Figure 3:
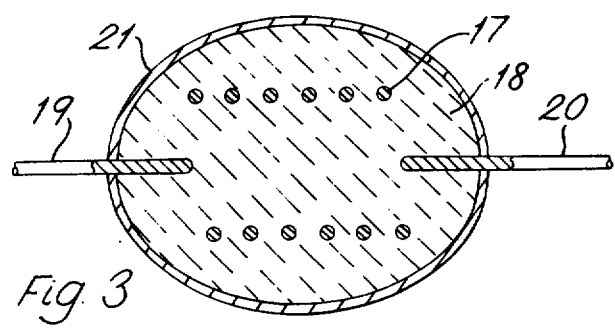
FIG. 3 shows in section a third form of gas-sensitive element.

FIG. 3 shows yet another type of gas-sensitive element in which a heating coil 17, consisting for example of platinum or platinum-rhodium wire, is embedded in a bead 18 of an inert refractory material such as alumina, except for its free ends 19 and 20; the coil 17 is suitably of similar form to the coils 10 and 13, and the bead 18 may suitably be formed around the coil 17 in the manner described in British Patent Specification No. 892,530. The coil 17 in this case serves only as a heating and measuring wire and does not cause catalytic oxidation; for example, as will be seen from Table II, the temperature at which an alumina-encapsulated platinum-rhodium wire causes catalytic oxidation of carbon monoxide is considerably higher than that for such a wire encapsulated in fused glass. On the surface of the bead 18 is a layer 21 of an appropriate platinum-rhodium alloy.

When a heating current is passed through the coil 17 so that the bead 18 and alloy layer 21 are raised sufficiently in temperature, the layer 21 when exposed to an oxygen-containing atmosphere will cause combustion of carbon monoxide at a temperature lower than the temperature at which it can readily cause combustion of hydrogen. By selection of the temperature, the layer 21 can be used to detect the presence of carbon monoxide, even in the presence of hydrogen, by sensing the change in resistance of the coil 17 due to the heat of the relevant catalysed reaction.

Figure 4:
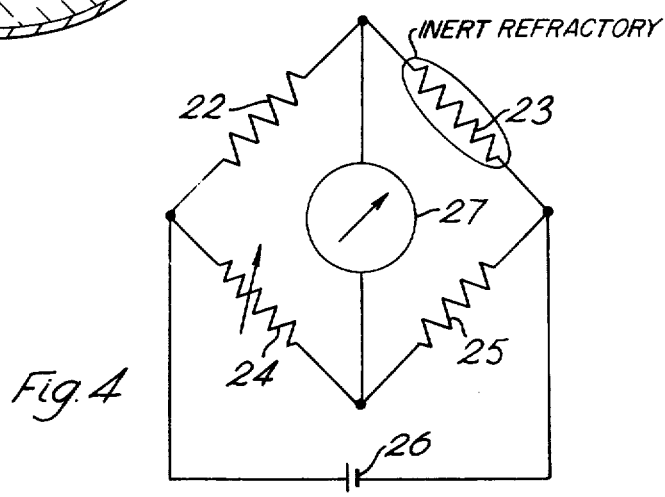
FIG. 4 is a diagram of an electrical circuit in which these three forms of element may be used.

In FIG. 4 is shown in basic form a Wheatstone bridge circuit suitable for use with any of the types of element shown in FIGS. 1, 2 and 3. The four arms of the bridge are respectively constituted by a sensing resistor 22 consisting of the coil 10, 13 or 17 of the relevant gas-sensitive element, a compensating resistor 23 having a resistance approximately equal to that of the resistor 22, a variable resistor 24, and a fixed resistor 25 having a value such that the bridge can be balanced by adjustment of the resistor 24. Across the two diagonals of the bridge are respectively connected a voltage source 26 and a current meter 27, the voltage of the source 26 being chosen so that the current passing through the resistor 22 will be such as to heat the gas-sensitive element to a desired operating temperature when the bridge is balanced; the resistor 23 will of course then be heated to approximately the same temperature. The compensating resistor 23 may suitably be in the form of a coil of wire substantially identical to the coil which constitutes the sensing resistor 22 and embedded in a bead of an inert refractory material; a suitable material for the bead is alumina containing about 5% (by molecular proportion) of magnesia, the presence of the magnesia ensuring that the bead will be of low porosity. It will be appreciated that the structural form of such a compensating resistor will be substantially the same as that of the element shown in FIG. 3, but without the layer 21.

In use the gas-sensitive element and the compensating resistor 23 are heated to the required temperature and an atmosphere to be tested is brought into contact with them, in a similar manner for the two devices; systems using gas flow or diffusion to effect such contact are well known in the art, and need not therefore be described here. The bridge circuit is initially calibrated with the gas-sensitive element and the compensating resistor 23 in contact with air while heated to the desired operating temperature, the bridge being balanced, as indicated by zero deflection of the meter 27, by appropriate adjustment of the resistor 24. Thus, when carbon monoxide is present in the atmosphere under test, the increase in temperature of the gas-sensitive element caused by the combustion on it of carbon monoxide will result in an increase in the resistance of the resistor 22, but no corresponding increase will occur for the resistor 23. The bridge will thus go out of balance, the resulting deflection of the meter 27 giving an indication of the carbon monoxide concentration. The use of the compensating resistor 23 is of course desirable to take account of possible fluctuations in parameters such as the voltage of the source 26 and the temperature and flow rate of the atmosphere under test.

Gas-sensitive elements of the types shown in FIGS. 1, 2 and 3 can of course also be used in arrangements of the kind in which the temperature of the element is maintained substantially constant at an appropriate value by automatic variation of the current flowing through the relevant coil, the magnitude of the necessary current providing an indication of the carbon monoxide concentration in an atmosphere brought into contact with the element; in such an arrangement it is convenient also to use the resistance of the coil as the parameter to which the automatic control system for the current responds. In other systems in accordance with the invention the temperature of the catalyst may be sensed by different types of thermometric device, for example employing thermocouples or thermistors.

We claim:
1. A method of testing an oxygen-containing atmosphere for the presence of carbon monoxide, the method comprising:
   bringing said atmosphere into contact with a catalyst consisting of a platinum base alloy containing rhodium in a proportion of not less than about 10% by weight while maintaining said catalyst at a temperature such that it is capable of causing combustion of carbon monoxide but will not readily cause combustion of hydrogen in said atmosphere; and
   sensing any thermal effect on said catalyst caused by the occurrence thereon of a combustion reaction.
2. A method according to claim 1, in which said alloy contains about 40% by weight of rhodium.
3. A method according to claim 1, in which said atmosphere is produced by mixing air with an exhaust gas mixture resulting from a combustion process.
4. A method according to claim 1, in which said atmosphere contains at least 10% by volume of oxygen and the hydrogen concentration in said atmosphere is less than one tenth of the oxygen concentration.
5. A method according to claim 1, in which said catalyst is in the form of a wire which is heated to said temperature by the passage through it of an electric current.

6. A method according to claim 5, in which said wire has been subjected to a pretreatment involving heating it to a temperature in the range 900°–1200° C for at least five minutes.

7. A method according to claim 5, in which said alloy contains about 40% by weight of rhodium and said temperature lies in the range of about 150 to 270° C.

8. An apparatus for use in gas detection, the apparatus comprising:

- a Wheatstone bridge circuit in adjacent arms of which are respectively connected similar resistors respectively constituted by first and second coils of wire each consisting of a platinum base alloy containing rhodium in a proportion of not less than about 10% by weight, said second coil being embedded in a bead of an inert refractory material and said first coil and said bead being exposed for contact with an atmosphere to be tested;
- means for energising said bridge circuit, said energising means being operative to pass through said first coil when said bridge circuit is balanced an electric current such that when an atmosphere containing oxygen, carbon monoxide and hydrogen is brought into contact with said first coil it will cause combustion of carbon monoxide but will not readily cause combustion of hydrogen; and
- means responsive to an out-of-balance condition of said bridge circuit.

9. An apparatus for use in gas detection, the apparatus comprising:

- a Wheatstone bridge circuit in adjacent arms of which are respectively connected similar resistors respectively constituted by first and second coils of wire each consisting of a platinum base alloy containing rhodium in a proportion of not less than about 10% by weight, said first and second coils being respectively embedded in a first bead of fused glass and a second bead of an inert refractory material and said first and second beads being exposed for contact with an atmosphere to be tested;
- means for energising said bridge circuit, said energising means being operative to pass through said first coil when said bridge circuit is balanced an electric current such that when an atmosphere containing oxygen, carbon monoxide and hydrogen is brought into contact with said first bead it will cause combustion of carbon monoxide but will not readily cause combustion of hydrogen; and
- means responsive to an out-of-balance condition of said bridge circuit.

* * * * *